United States Patent
Baumgart et al.

(10) Patent No.: US 6,914,683 B1
(45) Date of Patent: Jul. 5, 2005

(54) MEASUREMENT OF SMALL, PERIODIC UNDULATIONS IN SURFACES

(75) Inventors: Joerg Baumgart, Salem-Mimmenhausen (DE); Norbert Rau, Kirchheim (DE); Horst Truckenbrodt, Ilmenau (DE)

(73) Assignee: DaimlerChrysler AG, Stuttgart (DE)

( * ) Notice: Subject to any disclaimer, the term of this patent is extended or adjusted under 35 U.S.C. 154(b) by 0 days.

(21) Appl. No.: 09/807,125

(22) PCT Filed: Sep. 7, 1999

(86) PCT No.: PCT/EP99/06591

§ 371 (c)(1),
(2), (4) Date: Oct. 10, 2001

(87) PCT Pub. No.: WO00/22377

PCT Pub. Date: Apr. 20, 2000

(30) Foreign Application Priority Data

Oct. 8, 1998 (DE) .......................... 198 46 302

(51) Int. Cl.[7] .......................... G01B 11/02; G01B 11/30; G01N 21/00
(52) U.S. Cl. ................ 356/512; 356/237.2; 356/237.1; 356/600
(58) Field of Search ................... 356/512, 445, 356/600, 237.2, 237.5, 237.1

(56) References Cited

U.S. PATENT DOCUMENTS

| | | | |
|---|---|---|---|
| 3,782,827 A | | 1/1974 | Nisenson et al. ........... 356/120 |
| 3,850,526 A | | 11/1974 | Corey, III ................... 356/109 |
| 3,877,814 A | * | 4/1975 | Hess et al. ................... 356/613 |
| 4,715,709 A | * | 12/1987 | Sekine et al. ............ 356/237.2 |
| 4,866,287 A | * | 9/1989 | Weber ................... 250/559.18 |
| 5,179,425 A | * | 1/1993 | Reinsch et al. ............. 356/600 |
| 5,189,490 A | * | 2/1993 | Shetty et al. ............... 356/600 |
| 5,488,476 A | * | 1/1996 | Mansfield et al. .......... 356/512 |
| 6,249,351 B1 | * | 6/2001 | de Groot ..................... 356/512 |

FOREIGN PATENT DOCUMENTS

| | | |
|---|---|---|
| EP | 0 585 839 A2 | 8/1993 |
| JP | 01-292202 | 11/1989 |
| JP | 03-295408 | 12/1991 |
| JP | 07-159344 | 6/1995 |

OTHER PUBLICATIONS

*Light Transmission Optics*, Second Edition, Dietrich Marcuse (1929) p. 52–55.
*Diffraction of light from optical disks*, 2417 Optical Engineering 34 (1995) Apr. No. 4, Bellingham, Wash, US Haiming Wang, pps 1098–1104.
PCT International Search Report and translation of pertinent portion.
Yamatake et al., Method and Apparatus for Inspection of Irregular Surface, Translation of Japanese Kokai Patent application No. Hei 3[1991]–295408, US Patent Trademark Office translation on March 2004 of Japanese application dated Dec. 26, 1991.*

* cited by examiner

*Primary Examiner*—Russell Adams
*Assistant Examiner*—Andrew Sever
(74) *Attorney, Agent, or Firm*—Crowell & Moring LLP (57) ABSTRACT

In a method and apparatus for detecting small periodic wave patterns in technical surfaces, monochromatic coherent primary light is directed onto a workpiece surface approximately at right angles to the expected periodic wave patterns, and at an angle of incidence that grazes the workpiece surface, creating a diffraction image of the waved surface structure in the secondary-light beam. The occurrence of two intensity maxima immediately indicates the presence of a periodic wave pattern, whose period is evaluated through inverse proportionality from the spacing of neighboring intensity maxima, while the depth of the wave troughs is determined from the intensity of neighboring intensity maxima and from the period. The intensity distribution in the diffraction image in the secondary-beam path is subjected to an autocorrelation, and both the period and the depth of the wave pattern can be calculated from the autocorrelation function.

13 Claims, 5 Drawing Sheets

MEASUREMENT OF SMALL, PERIODIC UNDULATIONS IN SURFACES

BACKGROUND AND SUMMARY OF THE INVENTION

This application claims the priority of PCT International Application No. PCT/EP99/06591, filed Sep. 7, 1999 (07.09.99) and German patent document 198 46 302.2, filed Oct. 8, 1998, the disclosure of which is expressly incorporated by reference herein.

The invention is directed to a method and apparatus for detecting and measuring small periodic wave patterns in technical surfaces, of the type disclosed, for example, by U.S. Pat. No. 3,850,526.

On finely processed workpiece surfaces, it is possible to observe unintended wave patterns of the type of interest here, with a period up to about 1.5 mm; and the possibility exists that there may be even longer periods for wave patterns of the type in question. Accordingly, the term "small wave patterns" will be used here to denote those having a spacing between the wave-structure peaks smaller than two millimeters, although in most cases the periods are significantly less than one millimeter.

For reliable sealing at points where shafts pass through housing walls, in addition to the sealing ring provided with an annular radial sealing lip, it is also necessary to take into account the properties of the opposed running surface on the shaft. To produce a smooth surface at such shaft journals, they may be circumferentially ground, finished on a lathe, burnished, rolled or externally abraded. Besides specific roughness values, the manufacturer of the shaft journal also prescribes the degree to which the surface is free from torsion. Torsion-free, for example in the case of ground surfaces, means that the ground structure lies precisely in the circumferential direction and there are no superimposed regular wave components. However, in modern mass production it is not only difficult to create technical surfaces reproducibly without torsion, but problems are also encountered in reliably detecting such freedom from torsion and, where necessary, quantifying any torsional structure.

German patent document DE 197 40 141 A1 describes a mechanically operating test-score method for detecting and quantifying torsional structures or wave patterns that are of interest here, permitting reliable and quantitatively comprehensive information concerning virtually all relevant parameters of the torsional structure. The known test-score method gives usable results, in particular even if the wave pattern is not very pronounced and/or has a strong stochastic roughness component superimposed on it, when the stochastic roughness component has been substantially removed by means of an autocorrelation of the surface data. However, the known method of generating the surface data is very time-consuming and must be carried out very carefully. This method cannot therefore be used to monitor directly the manufacturing of technical surfaces. Instead, this method can be used as a reference method to control other torsional determination methods.

German patent document DE 198 09 790 A1, which was published after the priority date of the present patent, describes a contactless, optical method in which the raw data of the surface to be analyzed are obtained from direct, magnified imaging of a small segment of the surface. The method operates with arbitrary light as the primary-light type. The illuminated surface is sharply focused on a matt panel or on a high-resolution photodiode array by the use of imaging optics. In this method, coarse and strongly inclined torsional structures can be detected directly from the visual appearance of the image, without further processing of the image data. Such strongly pronounced torsional structures, however, can be detected by a trained eye anyway, i.e. merely with suitable illumination and with the aid of a lens. Such coarse cases generally occur rarely in practice, and do not cause problems with regard to their detection. For less pronounced and/or less inclined torsional structures, however, according to the this method it is necessary to generate image-data records of a plurality of neighboring surface parts, and to combine them as a function of position to form a uniform image-data record, each individual image-data record being respectively subjected beforehand to a Radon transformation.

Although the torsional determination method in German patent document to DE 198 09 790 A1 operates faster than the test-score method, it nevertheless also requires some degree of care since, on the one hand, the reference position of the workpiece with respect to the measuring instrument must be known accurately and, on the other hand, the measuring device and the workpiece must be held exactly stationary relative to each other during the measurement. In the known relative position of the workpiece axis and the measuring instrument, it is necessary to take a plurality of recordings in close succession, which is also time-consuming and requires care. Furthermore, the evaluation also requires some degree of care and supervision since the individual images must be matched to one another with a view to uniform average grey-scale distribution. The known method does provide information about the spacing of the wave patterns and their inclination with respect to a reference direction. However, information about the depth of the wave patterns and their cross section cannot be obtained directly using this method and can only be obtained with restrictions. The known method can be used in the laboratory to detect the presence or absence of surface torsion in a limited number of prepared workpieces, but the method is less suitable for use in manufacture.

U.S. Pat. No. 3,850,526, mentioned previously discloses a method and apparatus for the optical detection of periodic wave patterns in finely processed workpiece surfaces, in which the latter are illuminated with a beam of monochromatic, coherent light—primary light—and a diffraction image of the periodic wave patterns is produced in the secondary light returned by the surface. In this case, the primary light is directed onto the workpiece surface at a large angle of incidence with respect to the normal to the surface and approximately at right angles to the expected periodic wave patterns, and the intensity distribution of the diffraction image is evaluated. Of the beams involved (that is, the incident primary-light beam and the emerging secondary beam), one is kept at a fixed angle of at most 80° with respect to the normal to the surface, whereas the beam or evaluation channel of the other respective beam can be moved through a relatively large angle range around the position of the reflected beam. By means of a tilting beam arrangement, the strongest diffraction orders are fully detected and measured in terms of intensity profile. By comparing the intensity distribution of the diffracting light measured using a workpiece with intensity distributions obtained beforehand using various roughness standards, the surface roughness of the workpiece to be analyzed can be found. The known type of surface inspection is not, however, applicable to ground surfaces in which two different fine shape structures only one of which is of interest, are superimposed on each other. The diffraction image of the periodic wave patterns would have specular noise of the stochastic ground structures superimposed on it to the extent that it could not be identified and therefore could not provide useful information.

U.S. Pat. No. 5,189,490 discloses a normal roughness measurement using the scattered-light method, in which a primary-light beam is reflected by the surface to be analyzed, and the reflected secondary beam is scattered in a way characteristic of the roughness structure of the surface. Using this scattered-light method, which is widespread in principle and in different configurations and/or applications, neither diffraction by a periodic diffraction structure nor alignment of the primary light at right angles to the orientation of parallel processing tracks take place. The method disclosed by the cited document indirectly provides qualitative and quantitative useful information about the surface to be analyzed only after comparison of the actual pattern of the scattered-light cone, obtained from the specimen, with a large number of stored reference patterns produced beforehand using known patterns.

U.S. Pat. No. 3,782,827 discloses a very similar comparison method, which operates according to the scattered-light method, for determining the roughness structure of technical surfaces. This measurement method only supplies a certain actual pattern of a scattered-light distribution of the respective specimen. By similarity comparison with a large number of stored reference patterns, it is possible indirectly only to find useful information as to whether or not the analyzed specimen has a similar surface topography to a known sample.

It is an object of the invention to provide an improved, manufacturing compatible, method and apparatus of the generic type, which can perform a measurement quickly, conveniently and with reproducible information being obtained.

Another object of the invention is to provide such a method and apparatus in which exact relative alignment of the workpiece and the device is no longer necessary for the measurement result.

Still another object of the invention is to ensure sufficient stability of the measurement image, even in the event of relatively unstable handling both of the workpiece and of the device.

Finally, yet another object of the invention is to provide a single measurement which gives not only reliable quantitative information, as to whether a periodic surface wave pattern is "present" or "not present", but also qualitative information about the period and the depth of the wave pattern, where appropriate, with corresponding image-data evaluation.

These and other objects and advantages are achieved by the detection method and apparatus according to the invention, by providing monochromatic, coherent light which strikes the wave crests on the surface at right angles to their length at a large angle of incidence—approximately grazing incidence. By exploiting the diffraction by the waved surface structure as a diffraction grating, a diffraction image is produced and the intensity distribution therein is evaluated. Owing to the large angle of incidence of the light, the effect of the scattered light from the stochastic ground structure in the diffraction image is substantially eliminated. The diffraction image remains stable and stationary even if the degree to which the measuring instrument is held stationary relative to the workpiece varies. Furthermore, the quality of the diffraction image does not depend, within realistic limits, on the relative alignment of the workpiece and the measuring instrument.

The presence of a torsional structure can be detected immediately from the occurrence of a local intensity maximum in the scattered-light cone. The spacings of the wave crests can be deduced from the spacing of a plurality of maxima—where different diffraction orders are involved. In this case, the spacings of the intensity maxima vary approximately in inverse proportion to the wave-crest spacings. That is, a very close succession of wave crests causes widely spaced brightness maxima in the intensity distribution of the scattered-light cone, while the intensity maxima are closer together if the spacings of the wave crests are larger. It is even possible to deduce the depth of the wave troughs by evaluating the intensities of the different diffraction orders and the period. However, it is difficult to obtain information about the angular position of the wave patterns in relation to the exact circumferential direction in the present invention.

Before explaining the invention further, a few comments will be made regarding the terminology. On the one hand, there are repeated references to "primary light" and "secondary light" and, on the other hand, there are references to a "diffraction image" in the secondary beam. The term "primary light" used here means light which is sent onto the workpiece surface to be analyzed (that is, incident light). The "secondary light" is not, for instance, light due to a fluorescence phenomenon, but the light which is returned, scattered, diffracted or reflected by the workpiece surface. Furthermore, despite the fact that the term "diffraction image" is used, it should not be inferred that an image forming method or device is involved in the present case. The primary light is diffracted by the waved surface structure and an intensity distribution corresponding to the diffraction is created in the secondary beam. "Diffraction image" means the specific nature of the relevant intensity distribution of this diffraction. A pictorial representation of the "diffraction image" for evaluating this intensity distribution (e.g., by using lenses or the like which form images) is not only unnecessary but would be incorrect. The direct collection of the "diffraction image" on a matt panel is sufficient for the visual intensity evaluation.

Other objects, advantages and novel features of the present invention will become apparent from the following detailed description of the invention when considered in conjunction with the accompanying drawings.

DETAILED DESCRIPTION OF THE DRAWINGS

Figure 1:
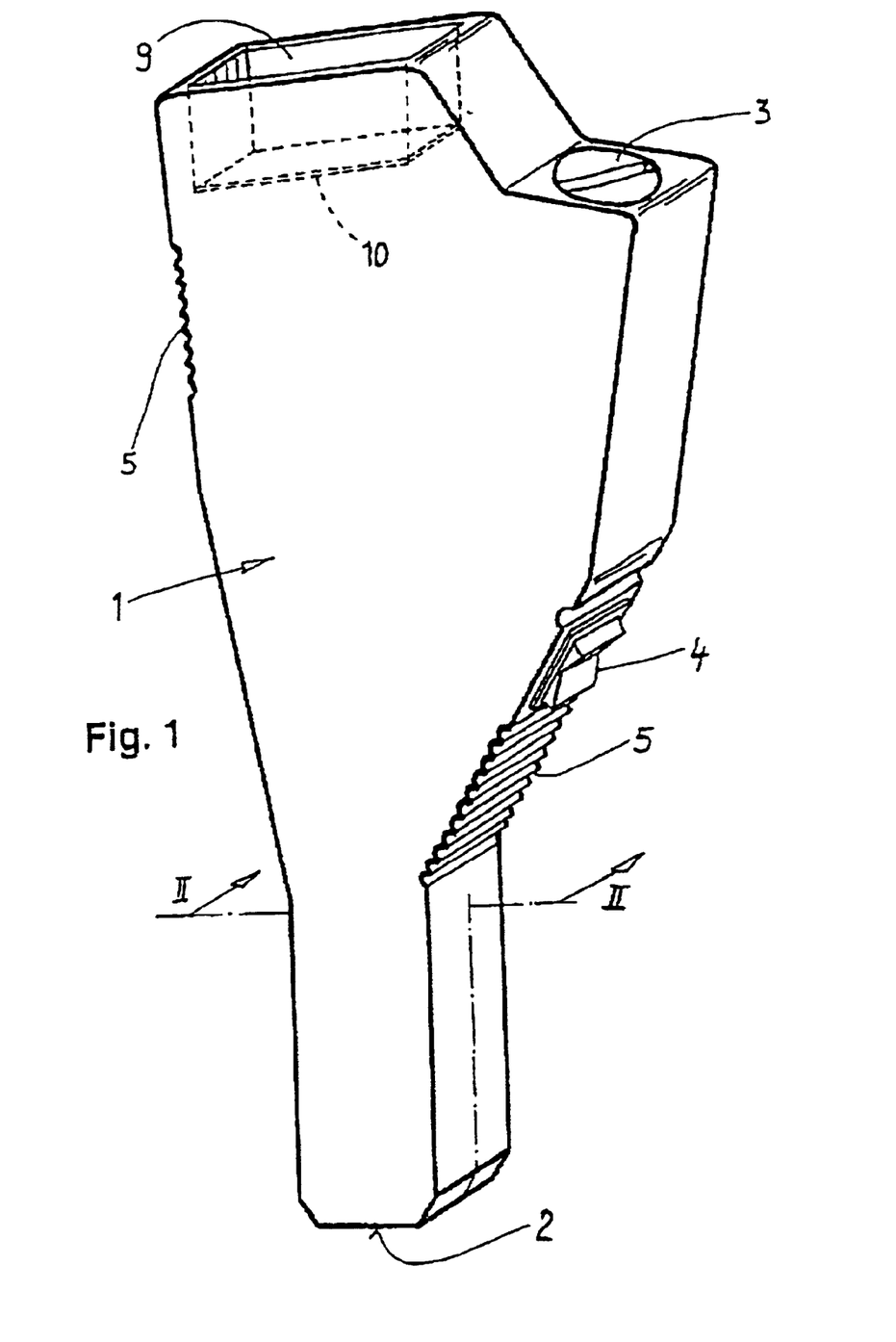
FIG. 1 shows a perspective representation of a handset according to the invention for inspection of workpiece surfaces with respect to periodic wave patterns by visual assessment of the secondary light.
Figure 2:
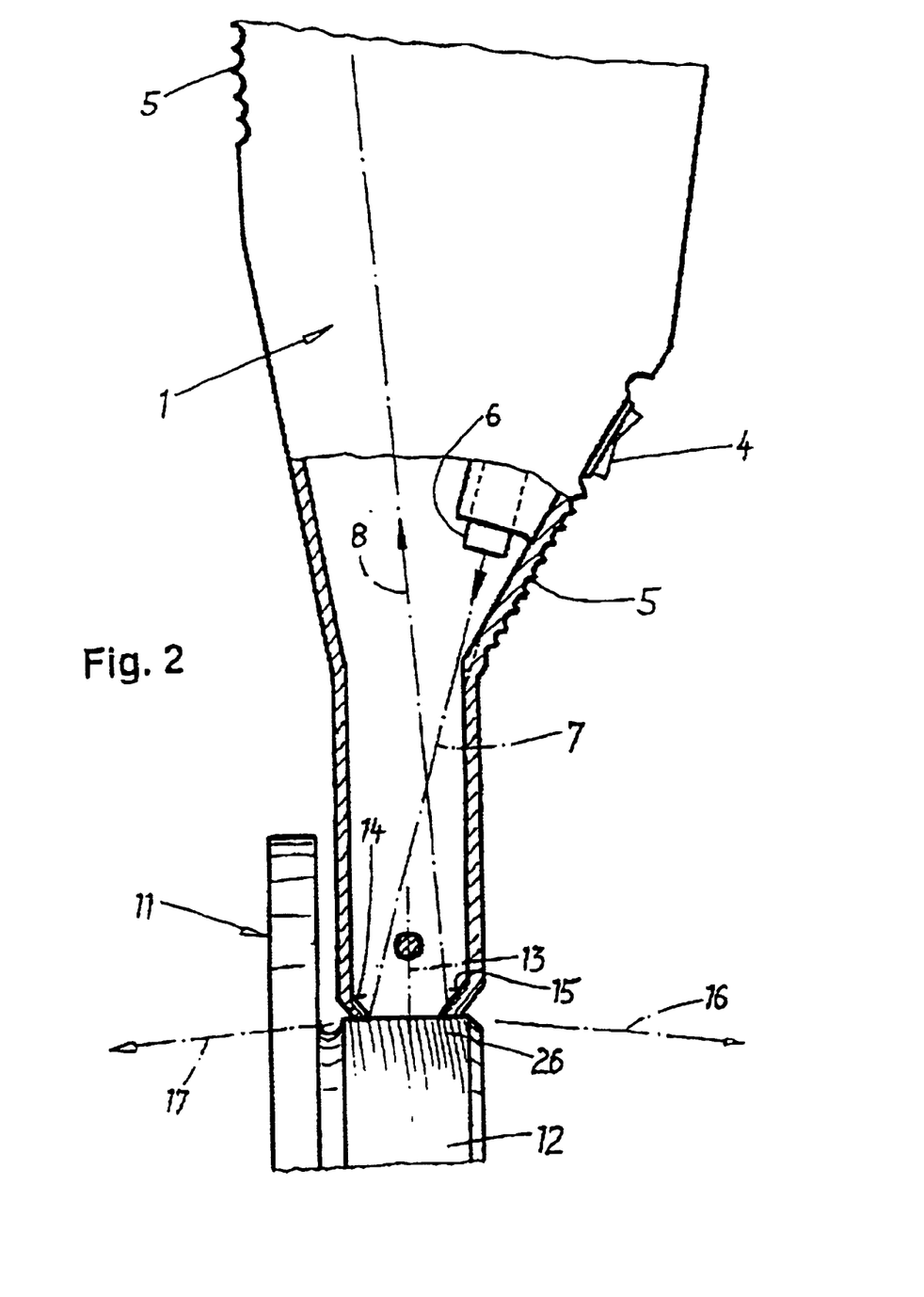
FIG. 2 shows a cross section through the lower part of the handset according to FIG. 1.

FIGS. 1 and 2 show a handset 1 for detecting small, periodic wave patterns 26 (FIG. 4 or 5) in the surface 12 of a workpiece 11 according to the scattered-light method. It is placed in a deliberate way on the workpiece surface 12 to be analyzed. A light pencil—light wave—emitted by a primary-light source is directed onto the workpiece surface in a specific direction and the scattered-light cone returned by the workpiece surface is collected in a secondary-light display of the meter.

In order to make the handset compatible with manufacture, and to be able to detect small, periodic wave patterns quickly and conveniently, and with reproducible information being obtained, according to the invention it is designed in the following way:

The handset 1, which is configured in an ergonomically expedient way and is provided with a lightweight plastic housing, is handy and, because of the mode of operation according to the invention, it can also be guided manually and nevertheless delivers measurement images which are positionally stable. As shown in FIG. 2, a laser diode 6 with integrated collimation optics, which is built into the handset as a primary-light source, emits a monochromatic, coherent primary-light beam 7. In principle, a He/Ne laser could also be used as the primary-light source, although this is not as compact as a laser diode and is not recommendable here for handsets of the proposed type, on grounds of size. A power corresponding to protection class I for low-power laser devices is sufficient for the present purposes. A battery compartment which can be closed by a flat-head screw 3 is integrated in the handset. The Mignon cell which it holds delivers the energy for the primary light, which can be switched on and off as required using a switch 4 arranged next to a knurled ribbed surface 5 so that it can be gripped easily.

In the region where the primary-light beam 7 emerges from the handset 1, an application surface 2 for placing the device on the workpiece surface 12 to be analyzed is provided on the device housing. Since the intention is to carry out analysis on relatively curved as well as flat surfaces, in the illustrated exemplary embodiment the application surface is of flat configuration and is reinforced by a small steel plate which encloses the exit window. In the region of this exit window, the deviating mirror 14 deflects the primary beam 7 so that it strikes the workpiece surface 12 to be analyzed at approximately grazing incidence (incidence direction 16) when the meter 1 is placed properly on the workpiece 11. To be precise, the primary-light beam 7 strikes the workpiece surface 12 to be analyzed at a specific, larger angle of incidence which—measured from the normal 13 to the surface—may lie in the range of about 75–88 degrees, preferably about 83±2 degrees. Because of the flat configuration of the handset application surface 2, after placing on the workpiece surface it can be aligned with respect to the primary beam 7 at least approximately at right angles to any expected periodic wave patterns 26 of the workpiece surface 12, by slight tilting of the device about the height axis. In the secondary-light region—apart from a deviating mirror—no installed optical parts (that is, no imaging or focusing optics or the like, for example) are provided in the handset. The secondary-light display directly collects the diffraction image caused by the primary light on the waved structure of the workpiece surface. The intensity distribution of the diffraction image is evaluated in order to detect any periodic wave patterns in the workpiece surface.

Since the wave patterns to be picked up on usually cylindrical workpiece surfaces are oriented in the circumferential direction, the axis of the incident primary beam must lie at least approximately in a plane which includes the cylinder axis. In order to make it possible to place the handset properly in the axial direction (FIG. 2) on relatively short and set-back component surfaces, the handset must be configured in a space-saving way in the region of the exit window. The primary beam 7 and the secondary beam 8 (FIG. 2) are therefore space-savingly bent in the handset in such a way that the front primary-beam component and the rear secondary-beam component are essentially aligned at right angles to the workpiece surface 12. To that end, a small deflecting mirror 14 for the primary beam and another small deflecting mirror 15 for the secondary beam are arranged laterally at the boundary of the exit window, i.e. at a small distance from the point where the primary beam 7 strikes the workpiece surface.

In the illustrated exemplary embodiment, in order to make it possible to give the lower part of the housing, the beam shaft, a particularly short configuration as viewed in the axial direction of the component 11, the deflecting mirrors 14, 15 are arranged in such a way that the beam component of the primary beam 7 located in front of the primary-beam deflecting mirror 14, on the one hand, and the beam component of the secondary beam 8 located behind the secondary-beam deflecting mirror 15, on the other hand, cross each other at a relatively small angle. This beam arrangement makes it possible not only to achieve an especially space-saving construction design in the front part of the handset, but it is also thereby possible to minimize the number of beam deflections required, which besides minimal loss of luminous efficiency, not only provides cost and weight advantages but also maintenance and adjustment advantages.

Instead of the deflecting mirrors, it is also possible to use a deflecting prism. Optionally, the deflecting prism could advantageously be combined to form a stable module with the said reinforcing plate for limiting the exit window.

In the handset 1, the secondary-light display is designed as a matt panel 10 (FIG. 1) which makes the intensity distribution of the diffraction image immediately visible, so that it can be visually assessed and even preliminarily evaluated. The intensity distribution of the diffraction image, which can be seen on the matt panel, stays steady on the matt panel even if there is some degree of manual movement for the workpiece and/or for the handset. In order to shut out interfering extraneous light, the matt panel is arranged set-back at the bottom of an observation shaft 9. The latter may also be used to fit a photodetector or a digital camera to the handset.

For quantitative evaluation of the diffraction image, the intensity therein must be measured. To that end, a photodetector linear array or a photodetector matrix should be provided. Such a photodetector is not provided in the exemplary embodiment represented in FIGS. 1 and 2. It is, however, conceivable to provide such a photodetector instead of the matt panel 10. Suitable examples for this include CCD linear arrays or CCD matrices, spectrometer linear arrays or matrices, other photodiode linear arrays or matrices or the like. In this case, however, it would be expedient if a matt panel, on which the intensity distribution of the diffraction image can be directly collected and perceived, and a photodetector of the type which can be used to measure the intensity distribution of the diffraction image as a function of position, are both arranged in the secondary-light display. This being the case, the secondary-beam path may be delivered to the matt panel, on the one hand, or the photodetector, on the other hand, either simultaneously—by means of a beam splitter—or successively by means of a tilting mirror.

The intensities measured by the photodetector may be evaluated using a computer which is provided. Another possible way of evaluating and displaying the measurements is to couple the photodetector with a digital signal processor and an LCD display. The advantage of the latter variant involves compact design of the measuring instrument, including the associated data-processing system, without an additional computer unit.

Figure 3:
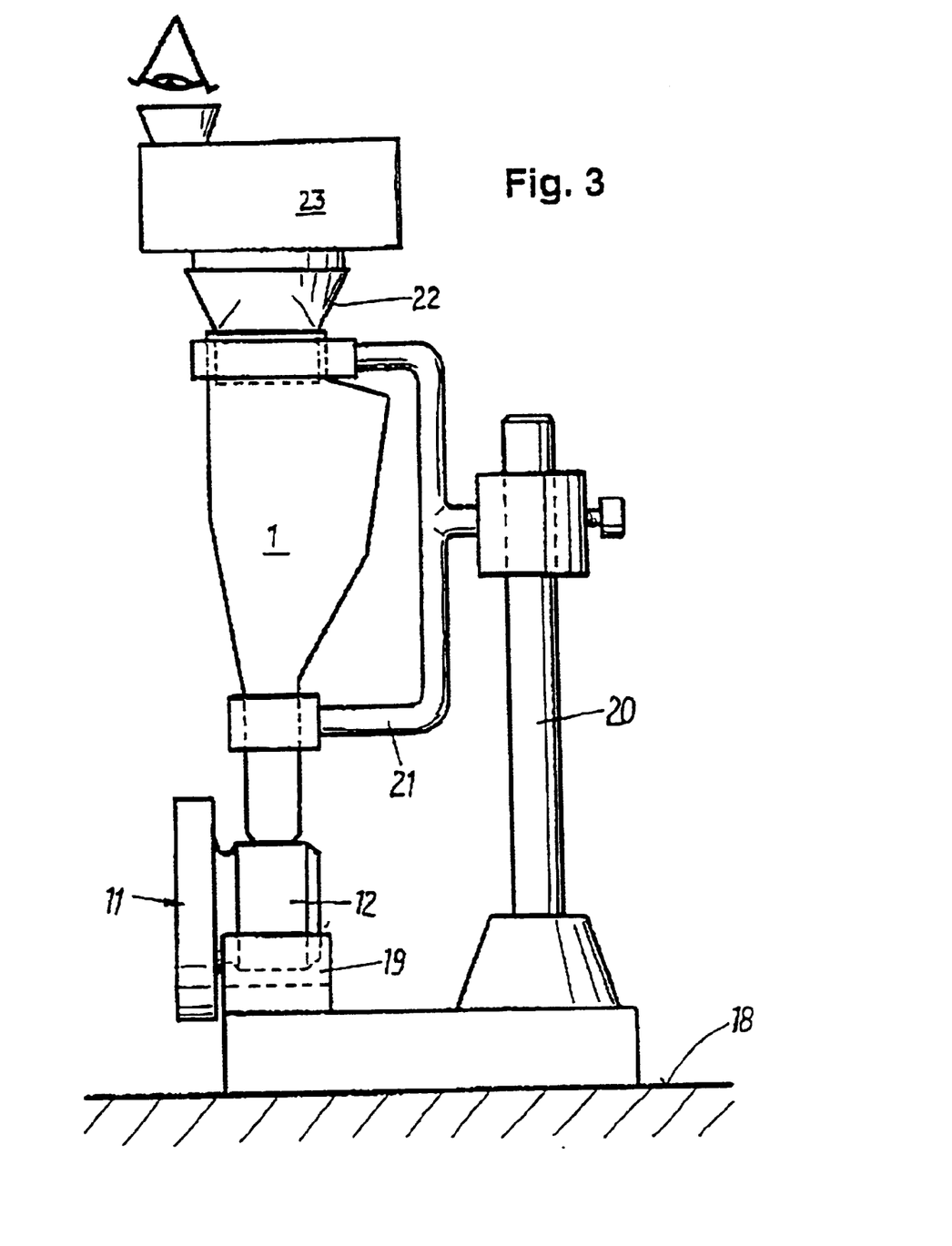
FIG. 3 shows a handset according to FIG. 1 which is held in a stand above a workpiece mount and has a digital camera connected via an adapter.

FIG. 3 represents yet another possible way of controlled evaluation of the secondary light, which also uses the handset. In this case, the handset 1 is held stationery by means of a holding device 21 and a stand 20 on a table 18, above an insertable prism 19 for a workpiece 11. An adapter 22, by which a digitally operating camera 23 is fitted to the handset, is placed stably in the observation shaft 9 of the handset 1. (See FIG. 1.) The digital camera, which carries the adapter 22 instead of its objective lens, may be lifted off or fitted on the handset as required. The matt panel needs to be removed when the digital camera is fitted on. The secondary light can then be observed in the viewfinder of the digital camera. With the recording technique of the digital camera, the intensity distribution of the diffraction image of the secondary-beam path 8 can be recorded and stored, as a data-processable record of the image data, on a special data medium which is integrated in the camera but can be removed.

The recorded image data can be forwarded in various ways from the manufacturing facility to an evaluation laboratory, from which the results (that is, the parameter values of the wave-pattern structure of the surface) can be sent back to the manufacturing facility. The image data can be sent on data medium (special camera-data medium), or—after downloading to a conventional floppy disk—on such a floppy disk as the data medium. The image data may, however, also be sent down a line to the evaluation laboratory by means of data transmission.

The procedure involved in the detection and, where appropriate, quantitative determination of the surface-wave patterns using the described device will be discussed in more detail below with reference to the surface structures according to FIGS. 4 and 5 which are represented in a greatly magnified and enhanced form. The macroscopic configuration of the e.g. circumferentially ground surface of the workpiece 11 (FIG. 4) or 11' (FIG. 5) is scarcely recognizable as a continuous surface in these detailed representations.

In this context, two topographical terms which are used here, namely "ground structure" in the sense of a superimposed stochastic fine structure, on the one hand, and periodic "torsional structure" or "wave pattern", on the other hand, will firstly be explained. Both terms relate to micro-deviations from the ideal macroscopic form of the surface, but the two microstructures differ with respect to the criteria of interest here, on the one hand by the extent or depth with which they occur on the workpiece. On the other hand, the two microstructures differ in a formal and statistical respect. The fine ground structures 24 (see FIG. 4), which are generally aligned precisely in the circumferential direction, have comparatively steep side edges but their cross section substantially occurs stochastically in other regards. Conversely, the torsional structures or wave patterns 26 observed are substantially flatter on the edges and have a relatively pronounced periodic shape component. A ground structure 24, which is formed by a plurality of small, stochastic indentations and has steeper edges and substantially smaller depth dimensions than the wave pattern, is typically superimposed on a periodic wave pattern or torsional structure 26.

Figure 4:
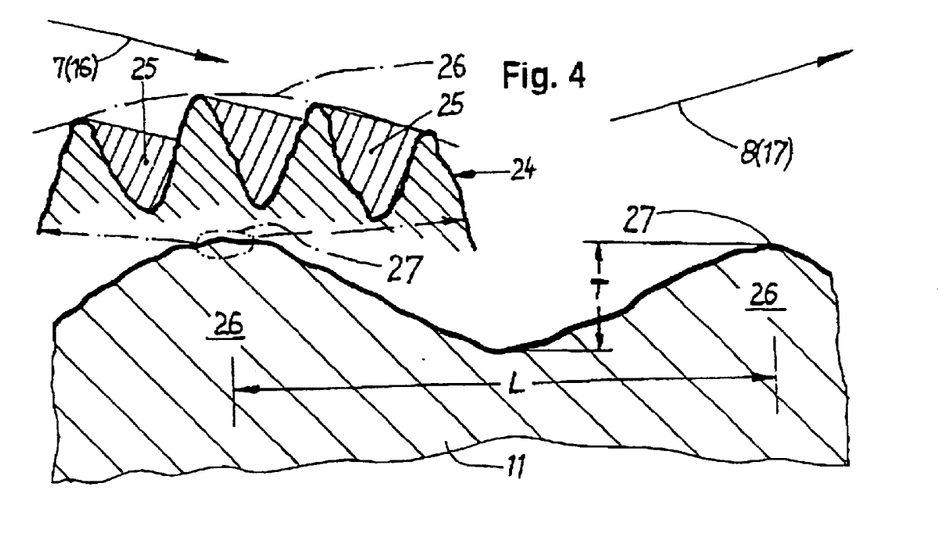
FIG. 4 shows a greatly enlarged and enhanced cross section through a small segment of a workpiece surface, in which a small segment is furthermore detailed with even greater enlargement.
Figure 5:
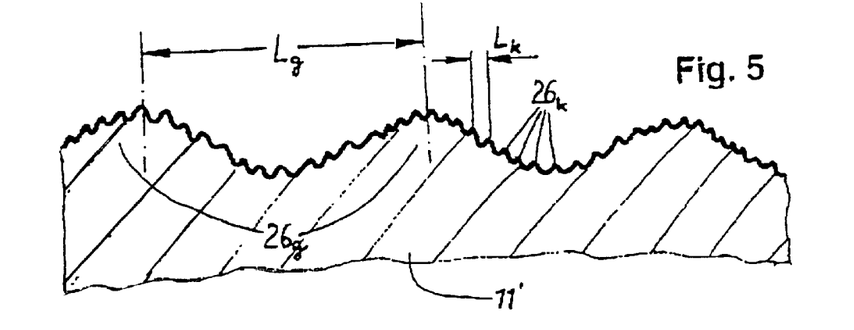
FIG. 5 likewise shows a greatly enlarged and greatly enhanced cross section through a segment of a different workpiece surface having two superimposed periodic wave patterns of different wavelength.

In the profile according to FIG. 4, waves 26 are arranged regularly, that is to say periodically next to one another. Because of the greatly enhanced representation of the roughness profile, the illumination direction 16 represented as an arrow is no longer angularly correct, i.e. the flatly incident primary radiation 7 still actually reaches the bottom of the troughs and the side edges of the wave patterns away from the light. With this approximately grazing illumination, however, the steeply cut indentations of the ground or fine structure 24 are substantially shadowed (shadow zones 25), so that they can only affect the returned light to a very small, virtually negligible extent. Conversely, the substantially flatter torsional structure 26 is substantially illuminated. Therefore, diffraction of the monochromatic and coherent primary light takes place substantially more strongly on the waved torsional structure than any superimposed diffraction on the ground structure 24. The zeroth diffraction order lies in the direction 17 of the secondary beam 8, which corresponds to that of the deviated direction reflected directly by the ideal macro-surface. If the surface is waved and diffraction occurs, then a further diffraction order, namely the first, can generally also be perceived at a certain spacing next to the zeroth diffraction order in the diffraction image.

The wavefronts which emerge from the various wave crests 27 and have stacked depths, interfere with one another and cause a diffraction image in the secondary light, only the zeroth and first diffraction orders of which can be seen as intensity maxima. If no periodic wave patterns are present on the surface, then no diffraction image is formed in the secondary light. In this case, two spaced intensity maxima cannot be perceived. A "reflective diffraction grating", that is to say a series of periodic waves in the surface to be analyzed, can therefore reliably be deduced from the occurrence of two different intensity maxima.

Other surface structures cause other intensity distributions in the secondary light. For example, an ideally reflective surface replicates the intensity distribution of the primary beam in the secondary beam as well. In such a case, only a single bright spot can be perceived in the secondary light. If there is a surface with entirely stochastic roughness and no periodic wave patterns, a uniform intensity distribution with a relatively pronounced specular structure will be observed.

At this point, for the sake of completeness, it should be mentioned that the bright spots appear as ovals which are relatively distorted in the axial direction according to the degree of the curvature of the cylindrical surface 12; in the case of smaller cylinder diameters, the major axis of the oval may be larger than the corresponding internal width of the matt panel, so that the bright spot appears as a bright line.

Figure 6:
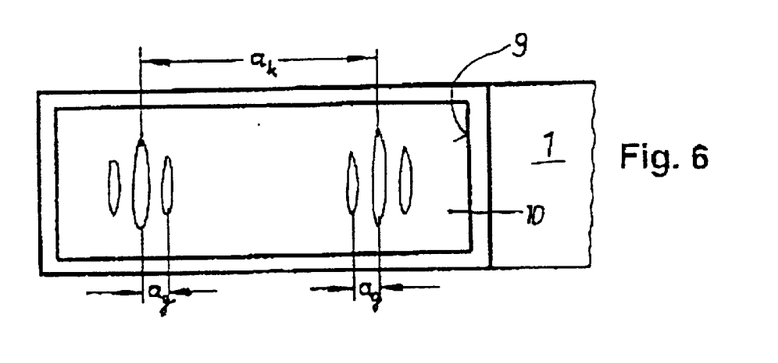
FIG. 6 shows the diffraction-image display which can be obtained when observing the workpiece surface according to FIG. 5 using the handset according to FIG. 1.

With reference to the example of the two FIGS. 5 and 6, the way in which the method according to the invention can also be used to deduce the period of the regular wave pattern will now be explained. The surface texture of the workpiece 11', which is represented on an enlarged scale in FIG. 5, has two superimposed periodic wave patterns with very different period, namely small waves $26_k$ with a small period $L_k$ and large waves $26_g$ with a large period $L_g$. If this surface is "observed" using the handset 1, the image shown in FIG. 6 appears on its matt panel 10. Two intensity maxima can be seen, which are resolved in strips and have a relatively large mutual spacing $a_k$, which is attributable to the small waves $26_k$. The individual strips of the two intensity maxima have a relatively small spacing $a_g$ from one another, which is associated with the wave pattern of the large waves $26_g$.

There is an approximate inverse-proportionality relationship between the spacing a of the intensity maxima within the diffraction image of the secondary light and the period L of the wave pattern: the smaller the spacing a of the bright spots is, the larger is the period L of the wave pattern, and vice versa. Using the equation $a \approx f/L$, the period L can be determined to good approximation from the spacing a of the intensity maxima. The factor f contained therein is an instrument constant, which needs to be empirically determined beforehand using known surface textures. Comparison of the measurement results according to the present invention, on the one hand, with reference samples whose period was determined according to the elaborate test-score method, on the other hand, has shown that the correspondence is very good and e.g. in the period range of from 70 to 110 $\mu$m a maximum error of $\pm 5$ $\mu$m is to be expected.

The spacing of the intensity maxima can immediately be determined, at least to rough approximation, on the matt panel 10. For example, the matt panel may be provided with a graduated scale and the spacing of the intensity maxima can be read off using it. If the graduated scale on the matt panel is movable, its zero point can be made to coincide with one of the intensity maxima, for example the brightest one, and then the spacing of the intensity maxima can be read off from the graduated scale. It might also be possible to gauge the spacing of the intensity maxima using a pair of dividers and to transfer this reading onto a ruler, or to gauge it directly using the legs of callipers. However, these simple methods are only recommendable with reservation, or as a preliminary method.

The handset 1 with visual evaluation of the secondary light is used for manual and retrospective inspection of finished workpieces, for example so that twisted workpieces can be rejected and sent back for reprocessing. This may be done by an inspector or by the supervisor of a production line on which torsion-free journal surfaces are intended to be produced. In general, visual and qualitative identification of the wave pattern itself, or a clear indication of its absence, is sufficient for the selection of torsion-free workpieces, whereas in this case it is less important to quantify the parameters of any wave pattern which is found.

As already mentioned above, the handsets may be equipped with "intelligent" photodetectors, which can also perform certain measurement and computation operations automatically. Handsets equipped in this way may output on a display at least the period L—and in the case of increased, integrated computation or evaluation power—also the depth T of any detected wave pattern. Although, without compromising their ease of handling, such handsets may also be equipped so that they can store identified parameter values if desired, such handsets are not generally conceived for storing large amounts of data.

It is also possible to use the wave-pattern measuring instrument according to the invention for automatic long-term monitoring of machine lines on which torsion-free journal surfaces are intended to be produced. In particular, those wave-pattern measuring instruments intended for constant use need to be equipped with an evaluation unit which measures and calculates the secondary light. Any production or error data which may be determined using a wave-pattern measuring instrument integrated in the manufacturing process should be collected, stored and evaluated in chronological order by a production-data logger or memory, in connection with other machine-operation data, inter alia such as e.g. the workpiece rotation speed, the grinding-head rotation speed, the grinding-head advance, the dressing advance, the workpiece number after the last dressing process in the case of circumferential grinding. From the large amount of data and the fact that wave patterns have or have not occurred, production experience can then be gained empirically and critical parameter pairings can be avoided. This online production monitoring using a powerful and continuous data memory may be integrated in the machine or may take place away from the immediate production line in a quieter room for production monitoring.

Figure 7:
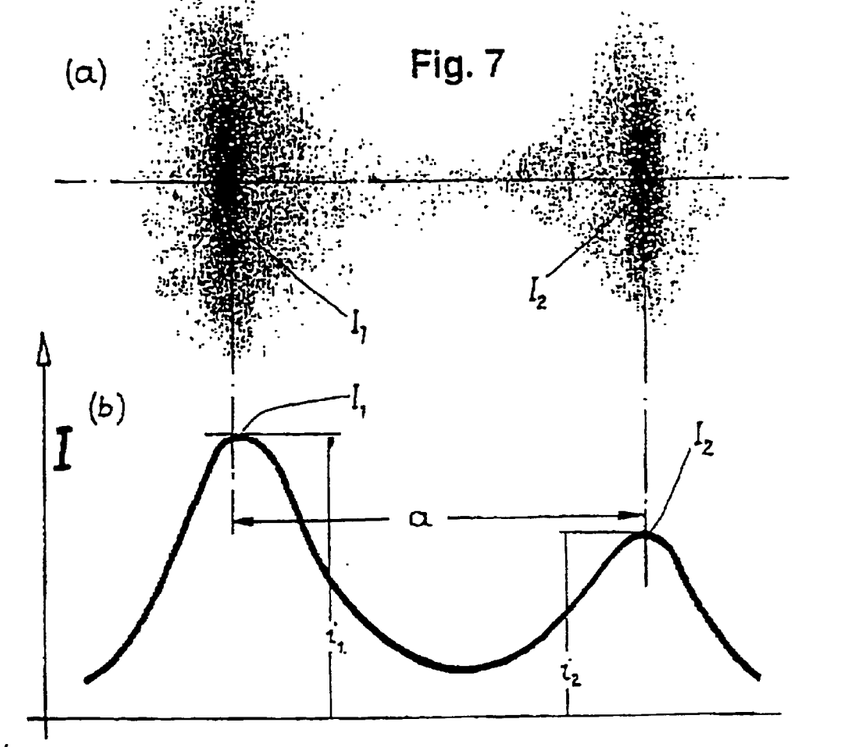
FIG. 7 shows, in the upper part (a) of the image, a two-dimensional brightness distribution of a diffraction image (represented in negative) and, in the lower part (b) of the image, a diagram corresponding thereto which represents the profile of the intensity along the line b—b in part (a) of the image.

During wave-pattern detection, the intensity distribution of the secondary light 8 over its cross-sectional area may be converted into a data-processable record of the image data, for example such as the one represented in negative at the upper part (a) of the image in FIG. 7. This image-data record may be evaluated with respect to the occurrence of intensity maxima $I_1$, $I_2$ in a correspondingly pre-programmed computer or in an "intelligent" photodetector integrated in the instrument, these being labeled as structural phenomena of the secondary light by the capital letters $I_1$, $I_2$. Conversely, the intensity values in these maxima are referenced by lower-case letters $i_1$, $i_2$.

Since not all the diffraction orders are represented as clearly as in FIG. 7, with two clearly recognizable intensity maxima, namely a main maximum $I_1$ of the zeroth diffraction order and a subsidiary maximum $I_2$ of the first diffraction order, but instead often have relatively strong specular noise superimposed on them, it is expedient first to subject the image data of the intensity distribution of the secondary light to an autocorrelation. In particular, less strongly pronounced torsional structures have stochastic roughnesses of approximately equal magnitude superimposed on them, so that an autocorrelation is particularly important in this case. The autocorrelation function represents a smoothing of the intensity profile in the diffraction orders, so that the maxima are readily detectable.

From the values of the autocorrelation function, e.g. at the positions of the zeroth and of the first diffraction orders, it is possible to determine the intensity values $i_1$ and $i_2$ in these diffraction orders. FIG. 7 shows the profile of such an autocorrelation function along a line b—b (see FIG. 7, part a) within the two-dimensional intensity distribution in the diffraction image. The spacing a of the two maxima $I_1$ and $I_2$, and the respective function value $i_1$ and $i_2$ of the autocorrelation function in the intensity maxima themselves, can be determined by computation—as mentioned.

As already mentioned above, the period L of the wave pattern can be calculated approximately according to a simple reciprocal relationship from the distance a which has been determined. However, the diffraction image also supplies depth-relevant information about the diffracting wave-pattern structure on the workpiece surface, this being due to the fact that not only the wave crests but also the wave troughs contribute to the creation of the diffraction image. For example, different diffraction images are obtained from two waved surfaces which have the same wave-pattern period as each other but a different wave-pattern depth from each other. The depth T of the wave troughs between the wave crests 27 (FIG. 4) can be deduced from the two intensity values $i_1$ and $i_2$ of the main and subsidiary intensity $I_1$ and $I_2$ while taking the period into account.

Figure 8:
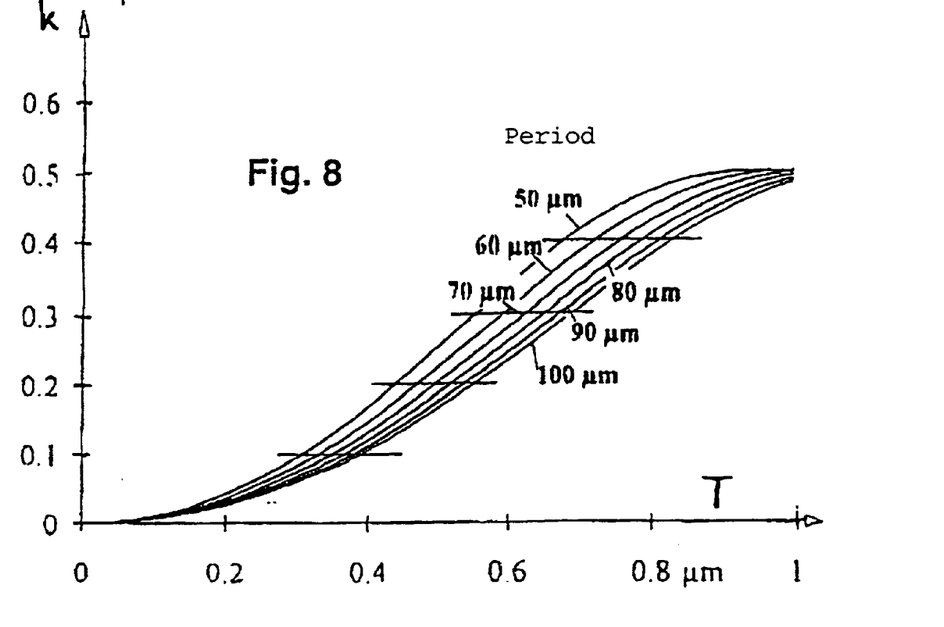
FIG. 8 shows a diagram which describes the relationship between an auxiliary variable k, determined from the intensity values $i_1$ and $i_2$, the period L of the wave pattern and the wave depth T, and is used to determine the wave depth T.

This calculation method is not quite as simple as the calculation of the period. In order to be able to determine the depth T of the wave troughs, it is first necessary to calculate a normalizing auxiliary variable k from the intensity values $i_1$, $i_2$ by using the equation $k=i_1 \times i_2/(i_1^2+i_2^2)$. This relationship—incidentally like the approximate reciprocal relationship mentioned above for the period L of the wave pattern—is valid if certain idealizing simplifications are applied, although these are readily available with the instrument design recommended in the present case. The auxiliary variable k tends towards zero for extremely low intensities. The brighter the first diffraction order is, and hence the closer its intensity is to the intensity of the zeroth diffraction order, the closer the auxiliary variable k will be to the "saturation" value of 0.5. Most practical cases will lie between the extremes just mentioned, that is to say in the maximum-spread range of the diagram lines in FIG. 8. By using this auxiliary variable and the period L which was already determined previously, the depth T of the wave troughs can be determined with the aid of the graph according to FIG. 8, which may also be stored as a data record in a computer and may be incorporated in the calculation.

Comparison of the results obtained in this way for the wave depth T with the values found using the test-score method shows a very good correlation. The depths determined according to the invention are, however, consistently somewhat lower than the reference values in the case of ground surfaces, specifically at about 62±5% of the reference values according to the test-score method. This difference is attributable to the different bandwidth limitations of the two methods. Although the test-score method also picks up details of the grinding topography, these details are suppressed in the case of grazing illumination. In the event that direct comparison is required, the depth values found according to the invention need to be multiplied by a correction factor (about 1.6 in the case of ground surfaces).

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method for detecting small periodic wave patterns in surfaces, comprising:
    illuminating a surface using a primary beam of monochromatic coherent light;
    directing said primary beam onto the surface at a large angle of incidence relative to a normal to the surface of the workpiece, and approximately at right angles to expected periodic wave patterns;
    generating a diffraction image of the periodic wave patterns produced in secondary light returned by the surface; and
    evaluating an intensity and spacial distribution of neighboring intensity maxima in the diffraction image; wherein,
        for separate determination of the wave pattern of a ground surface, in which the wave pattern has finer, steeply indented stochastic ground structures superimposed on it, the ground structures are shadowed by providing an approximately grazing incidence of the primary light beam onto the workpiece surface at a constant angle of incidence within an angular range of approximately 83±2°, whereby a diffraction image solely representing the wave patterns is produced because of an isolated illumination of the wave patterns thereby achieved, with primary light incident on their sides facing towards and away from the light and on respective wave crests.

2. The method according to claim 1, further comprising:
collecting the secondary light beam on a matt panel; and
visually evaluating its intensity distribution with respect to the occurrence of intensity maxima.

3. The method according to claim 1, further comprising:
measuring an intensity distribution of the secondary light as a function of position over an image area of the diffraction image; and
evaluating the measurements with respect to occurrence of intensity maxima.

4. The method according to claim 3, further comprising:
subjecting the intensity distribution of the secondary light to an autocorrelation; and
evaluating the autocorrelation function obtained therefrom.

5. The method according to claim 1, wherein:
spacing of neighboring intensity maxima is determined; and
period of the wave pattern is deduced therefrom.

6. The method according to claim 5, wherein:
intensity values of neighboring intensity maxima are determined; and
depth of wave troughs between wave crests is deduced therefrom and from the period of the wave pattern.

7. A device for detecting small periodic wave patterns in the surface of a workpiece, said device comprising a meter which is adapted to be placed in a defined way on the workpiece surface to be analyzed, with a primary-light source which directs a primary light beam of monochromatic, coherent light beam onto the workpiece surface in a predetermined direction, and a secondary-light display which collects a scattered-light cone returned by the workpiece surface in the meter, wherein:
    at least in a region where the primary-light beam emerges from the meter, it is directed in such a way that, when the meter is placed on the workpiece, it strikes the workpiece surface to be analyzed at an angle in the range of approximately 83±2°;
    the meter is designed so that, after placing on the workpiece surface, it can be aligned with respect to the primary beam at least approximately at right angles to any expected periodic wave patterns of the workpiece surface;
    the secondary-light display collects the scattered-light cone without imaging optics, as a diffraction image of a wave pattern; and
    an intensity distribution in the diffraction image is evaluated.

8. The device according to claim 7, wherein:
in an area to be applied to the workpiece surface, the device has an exit window;
deflecting elements for the primary beam and the secondary beam are arranged in a lateral periphery of the exit window; and the deflecting elements deflect the light beams such that a beam component of the primary beam located in front of the primary-beam deviating element and a beam component of the secondary beam located behind the secondary-beam deviating element are aligned approximately at right angles to the workpiece surface.

9. The device according to claim 8, wherein the optical deflecting elements are arranged in such a way that the beam component of the primary beam located in front of the primary-beam deviating element and the beam component of the secondary beam located behind the secondary-beam deviating element cross each other.

10. The device according to claim 7, wherein the secondary-light display comprises a matt panel which makes the intensity distribution of the diffraction image visually perceptible.

11. The device according to claim 7, wherein the secondary-light display comprises one of a linear and a two-dimensional matrix of a plurality of photoreceptive sensors which measure the intensity distribution of the diffraction image.

12. The device according to claim 7, wherein
both a matt panel, which makes the intensity distribution of the diffraction image visually perceptible, and one of a linear and a two-dimensional matrix of a plurality of photoreceptive sensors which measures an intensity distribution of the diffraction image, are arranged in the secondary-light display; and
the secondary-beam path is accessible via one of a beam splitter and a tilting mirror.

13. The device according to claim 12, further comprising a digitally operating camera which is fitted to the meter and positioned to record the intensity distribution of the diffraction image of the secondary-beam path.

* * * * *